United States Patent [19]

Jones et al.

[11] Patent Number: 5,091,558

[45] Date of Patent: Feb. 25, 1992

[54] NAPHTHALENE ANTI-PSORIATIC AGENTS

[75] Inventors: Gordon H. Jones, Cupertino; Michael C. Venuti, San Francisco; John M. Young, Redwood City, all of Calif.

[73] Assignee: Syntex (U.S.A.) Inc., Palo Alto, Calif.

[21] Appl. No.: 23,089

[22] Filed: Mar. 6, 1987

Related U.S. Application Data

[60] Continuation-in-part of Ser. No. 806,314, Dec. 9, 1985, abandoned, which is a division of Ser. No. 574,426, Jan. 27, 1984, abandoned.

[51] Int. Cl.$^5$ .............................................. C07C 69/00
[52] U.S. Cl. .................................. 560/139; 560/105; 560/107; 260/410.5; 514/550; 514/552; 514/533
[58] Field of Search ................... 560/139, 105, 107; 260/410.5; 514/550, 552, 533

*Primary Examiner*—Paul J. Killos
*Attorney, Agent, or Firm*—Brian Lewis; David A. Lowin; Tom M. Moran

[57] ABSTRACT

Psoriasis in mammals is relieved by topically administering naphthalenes of the formula:

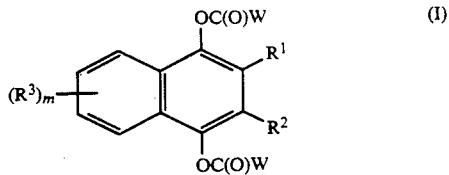

wherein:
$R^1$ is alkoxy, alkylthio, optionally substituted phenoxy or optionally substituted phenylthio;
$R^2$ is hydrogen, lower alkyl, optionally substituted phenyl or optionally substituted phenylalkyl;
$R^3$ is lower alkyl, lower alkoxy, or halo and m is 0, 1 or 2, or $R^3$ is optionally substituted phenyl, optionally substituted phenyl lower alkyl, optionally substituted phenyl lower alkoxy, amino, lower alkylamino, lower dialkylamino, cyano, or $S(O)_nR$ wherein R is lower alkyl; optionally substituted phenyl; optionally substituted phenyl lower alkyl; or optionally substituted heterocyclic aryl of three to nine ring atoms containing one or two heteroatoms selected from the group consisting of nitrogen, oxygen and sulfur, and the pharmaceutically acceptable acid addition salts thereof; and m is 1 and n is 0, 1 or 2; and
W is alkyl of one to seven carbon atoms, optionally substituted phenyl or optionally substituted benzyl.

37 Claims, No Drawings

NAPHTHALENE ANTI-PSORIATIC AGENTS

This is a continuation-in-part of U.S. Ser. No. 806,314 filed Dec. 9, 1985 (now abandoned) which in turn is a divisional of U.S. Ser. No. 574,426 filed Jan. 27, 1984 (now abandoned) which applications are incorporated herein by reference.

BACKGROUND OF THE INVENTION

1. Field of the Invention

The invention relates to naphthalene derivatives which are useful in inhibiting certain dermatological conditions. This invention also relates to pharmaceutical compositions useful in relieving the effects of certain chronic recurrent papulosquamous dermatoses, e.g., psoriasis. This invention also relates to a process for preparing compounds of this invention.

2. Related Disclosures

Psoriasis is a skin disease characterized in part by excessive proliferation of cells of the epidermis which remain strongly adherent and build up into a scaley plaque typical of the disease. Currently available therapies, which are not curative, depend on the control of epidermal cell proliferation through the use of hormonal agents, such as corticosteroids or through the use of compounds related to cancer chemotherapy such as hydroxyurea, methotrexate, and the nitrogen mustards.

While the above agents are effective to a certain extend, they cause numerous severe undersirable side effects including renal irritation, hepatic toxicity, and erythema.

The compounds, 2-methoxy-1,4-diacetyloxynaphthalene, 2-ethoxy-1,4diacetyloxynaphthalene and 2-methoxy-3-methyl-1,4-diacetyloxy-naphthalene known, but no useful biological activity has been ascribed to them. See J. Am. Chem. Soc. 48:2922-37 (1926) and Gazy. Chem. Ital. 73: 225-40 (1943). Certain naphthoquinones are known to be useful in treating psoriasis. See, for example, U.S. Pat. No. 4,229,478 and British Patent No. 1,243,401. But, these compounds have one or more drawbacks such as causing skin irritation, staining the skin and sensitizing the patient. Surprisingly, it has been discovered that the compounds of the instant invention are also effective antipsoriatic agents and are less irritating, do not stain the skin and do not sensitize when used in the treatment of psoriasis. Further, the compounds of the present invention are more stable in the topical formulations normally used.

SUMMARY

The present invention relates to a pharmaceutical composition in a form suitable for topical administration to mammals comprising a compound of the following formula

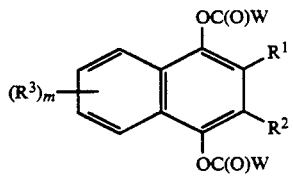

wherein:
$R^1$ is alkoxy of one to twelve carbon atoms, alkylthio of one of twelve carbon atoms, phenoxy or phenythio optionally substituted by one or two lower alkyl of one of four carbon atoms, lower alkoxy of one to four carbon atoms or halo;

$R^2$ is hydrogen, lower alkyl of one to six carbon atoms, phenyl or phenylalkyl optionally substituted by one or two lower alkyl of one to four carbon atoms, lower alkoxy of one to four carbon atoms or halo;

$R^3$ is lower alkyl of one to six carbon atoms, lower alkoxy of one to six carbon atoms, or halo and m is 0, 1 or 2 or $R^3$ is optionally substituted phenyl, optionally substituted phenyl lower alkyl, optionally substituted phenyl lower alkoxy, amino, lower alkylamino, lower dialkylamino, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2;and W is alkyl of one to seven carbon atoms, phenyl or benzyl optionally substituted with one or two lower alkyl of one to four carbon atoms, lower alkoxy of one to four carbon atoms or halo.

Another aspect of the invention is a method for relieving the condition of psoriasis in a mammal which comprises topically administering to said mammal a a psoriasis-relieving amount of a compound of formula (I).

Another aspect of the invention is the novel compounds of formula (I) wherein $R^1$, $R^2$, $R^3$, W, m and n are as defined above with the proviso that m is not 0 when $R^1$ is methoxy or ethoxy, $R^2$ is hydrogen and W is methyl or $R^1$ is methoxy, $R^2$ is methyl and W is methyl.

Yet another aspect of the invention is preparing compounds of formula (I) by reacting compounds of formula (IX)(infra) with an acid anhydride.

DETAILED DESCRIPTION AND PREFERRED EMBODIMENT

In its broadest aspect, the present invention relates to a pharmaceutical composition in a form suitable for topical administration to mammals comprising a compound of the following formula

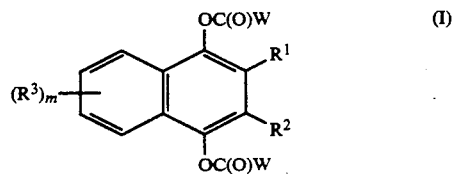

wherein:
$R^1$ is alkoxy of one to twelve carbon atoms, alkylthio of one to twelve carbon atoms, phenoxy or phenylthio optionally substituted by one or two lower alkyl of one to four carbon atoms, lower alkoxy of one to four carbon atoms or halo;

$R^2$ is hydrogen, lower alkyl of one to six carbon atoms, phenyl or phenylalkyl optionally substituted by one or two lower alkyl of one to four carbon atoms, lower alkoxy of one to four carbon atoms or halo;

$R^3$ is lower alkyl of one to six carbon atoms, lower alkoxy of one to six carbon atoms, or halo and m is 0, 1 or 2 or $R^3$ is optionally substituted phenyl, optionally substituted phenyl lower alkyl, optionally substituted phenyl lower alkoxy, amino, lower alkylamino, lower dialkylamino, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from eh group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2; and W is alkyl of one to seven carbon atoms, phenyl or benzyl optionally substituted with one or two lower alkyl of one to four carbon atoms, lower alkoxy of one to four carbon atoms or halo;

The present invention also relates to compounds of the formula

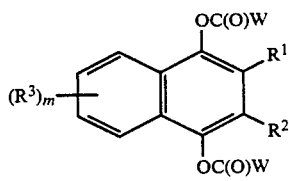

wherein:
$R^1$ is alkoxy of one to twelve carbon atoms, alkylthio of one to twelve carbon atoms, phenoxy or phenylthio optionally substituted by one or two lower alkyl of one to four carbon atoms, lower alkoxy of one to four carbon atoms or halo;

$R^2$ is hydrogen, lower alkyl of one to six carbon atoms, phenyl or phenylalkyl optionally substituted by one or two lower alkyl of one to four carbon atoms, lower alkoxy of one to four carbon atoms or halo;

$R^3$ is lower alkyl of one to six carbon atoms, lower alkoxy of one to six carbon atoms, or halo and m is 0, 1 or 2 or $R^3$ is optionally substituted phenyl, optionally substituted phenyl lower alkyl, optionally, substituted phenyl lower alkoxy, amino, lower alkylamino, lower dialkylamino, cyano, or $S(O)_nR$ wherein R is lower alkyl of one to six carbon atoms; optionally substituted phenyl; optionally substituted phenyl lower alkyl; or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano and the pharmaceutically acceptable acid addition salts thereof; and m is 1 and n is 0, 1 or 2; and W is alkyl of one to seven carbon atoms phenyl or benzyl optionally substituted by one or two lower alkyl of one to four carbon atoms, lower alkoxy of one to four carbon atoms or halo; with the proviso that m is not 0 when $R^1$ is methoxy or ethoxy, $R^2$ is hydrogen and W is methyl or $R^1$ is methoxy, $R^2$ is methyl and W is methyl.

More specifically, the present invention relates to compositions containing compounds of formula (I) wherein $R^3$ is in the 6-position and is hydrogen, bromo, chloro, fluoro or cyano.

an even more specific embodiment of the instant invention are compounds of formula (I) wherein $R^3$ is at the 6-position and is bromo, chloro, fluoro, cyano, methoxy, ethoxy, n-propoxy, i-propoxy, n-butoxy, and i-butoxy.

Within this specific embodiment of the instant invention, a preferred group of compounds of formula (I) are those wherein $R^1$ is lower alkoxy of one to three carbon atoms, $R^2$ is hydrogen and W is lower alkyl of one to five carbon atoms.

Another embodiment of the invention are compounds wherein $R^1$ is a phenoxy or phenylthio optionally substituted by one or two lower alkyl of one to four carbon atoms, lower alkoxy of one to four carbon atoms or halo.

Yet another embodiment of the invention are compounds wherein W is phenyl or benzyl optionally substituted by one or two lower alkyl of one to four carbon atoms, lower alkoxy of one to four carbon atoms or halo.

In the present specification and claims and term "alkyl" is intended to mean alkyl groups containing one to seven carbon atoms including straight chain groups, or branched chain groups. Illustrative of such groups are for example, methyl, ethyl, n-propyl, i-propyl, n-hexyl, 2-methylpentyl, and n-heptyl. The term "lower alkyl" refers to alkyl groups of one to six carbon atoms as defined above. Examples of "lower alkyl" groups are methyl, ethyl, n-propyl, i-propyl, n-butyl, i-butyl, s-butyl, 2,2-dimethylpropyl and t-hexyl. The term "phenyl lower alkyl" refers to an optionally substituted phenyl ring attached to an alkylene chain of one to six carbon atoms.

The term "lower alkoxy" refers to a straight or branched chain aliphatic group of one to six carbon atoms having bonded thereto an oxygen moiety. Examples of "lower alkoxy" are methoxy, ethoxy, n-propoxy, i-propoxy, n-butoxy, i-butoxy, s-butoxy, t-butoxy and n-pentyloxy. "Phenyl lower alkoxy" refers to a phenyl ring attached to an alkylene chain of one to six carbon atoms having bonded thereto an oxygen atom. Examples of "phenyl lower alkoxy" are benzyloxy, 4-chlorophenylethoxy and phenyl-n-propoxy.

The term "lower alkylthio" refers to a straight or branched chain aliphatic group of one to six carbon atoms having bonded thereto a sulfur moiety. Examples of "lower alkylthio" are methylthio, ethylthio, n-propylthio, i-butylthio an n-hexylthio.

Optionally substituted phenyl refers to a phenyl ring optionally substituted by one or more substituents selected from the group consisting of lower alkyl, lower alkoxy, halo, lower acyl, lower acyloxy, cyano, nitro, amino and lower acylamino unless otherwise defined.

The term "halo" refers to fluoro, chloro, and bromo. The term "cyano" refers to the group —CN. The term "amino" refers to the group —$NH_2$.

The term "lower alkylamino" refers to an amino group substituted by lower alkyl as is defined above. Examples of "lower alkylamino" are methylamino, ethylamino and n-butylamino.

The term "lower dialkylamino" refers to an amino group substituted by two lower alkyl groups. Examples of "lower dialkylamino" are dimethylamino, dipropylamino and methylethylamino.

The term "lower acyl" refers to the group R$^4$C(O)— wherein R$^4$ is a lower alkyl group of one to six carbon atoms or an optionally substituted phenyl group. Examples of "lower acyl" are acetyl, propanoyl, butanoyl and benzoyl. The term "lower alkoxycarbonylalkyl" refers to an ester group of the formula R$^5$OC(O)— substituted on an alkyl group wherein R$^5$ is lower alkyl as is defined above. Examples of "lower alkoxycarbonylalkyl" are methoxycarbonylmethyl, ethoxycarbonylmethyl, ethoxycarbonylethyl, propoxycarbonylethyl and the like.

The term "heterocyclic aryl" is defined as those cyclic aromatic compounds having 3 to 9 ring carbon atoms and having one or two heteroatoms in the ring selected from the group consisting of nitrogen, oxygen and sulfur. Examples of such include the groups thiapyranyl, benzothiapyranyl, furyl, pyrrolyl, imidazolyl, pyraxolyl, pyridinyl, pyrimidinyl, indolyl, quinolinyl, indazolyl and the like. These heterocyclic aryls may be optionally substituted with halo, lower alkyl, cyano and lower alkoxy.

By the term "pharmaceutically acceptable acid addition salts" as sued int he case of the various R$^3$ containing heterocyclic aryl substituents herein is intended to mean those non-toxic pharmaceutically acceptable acid addition salts which do not adversely affect the pharmaceutical properties of the parent compounds. With respect to these addition salts, suitable inorganic anions include, for example, chloride, bromide, iodide, sulfate, phosphate, nitrate, and the like. Suitable organic anions include, for example, acetate, benzoate, lactate, picrate, propionate, butyrate, valerate, tartrate, maleate, fumarate, citrate, succiante, tosylate, ascorbate, nicotinate, adipate, gluconate and the like.

FORMULATION AND ADMINISTRATION

The compositions of the present invention may be formulated for administration in any convenient way be analogy with other topical compositions adapted for use in mammals. These compositions may be presented for use in any conventional manner with the aid of any of a wide variety of pharmaceutical carriers or vehicles.

The naphthalenes of formula (I) may be formulated with suitable pharmaceutical vehicles known in the art to form particularly effective topical compositions. An effective amount of the naphthalene compound is about 0.001%w to about 10%w of the total formulated composition. The rest of the formulated composition will be about 90%w to about 99.999%w of a suitable excipient which may include a pharmaceutically acceptable solvent and other pharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powders, creams, ointments, lotions, gels, foams, aerosols, solutions and the like. Particularly suitable solvents include water, ethanol, acetone, glycerine, propylen carbonate, dimethylsulfoxide (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil or petrolatum and other typical pharmaceutical adjuvants such as anti-oxidants, antiseptics, or compatible adjuvants. A typical cream base formulation is as follows:

| | |
|---|---|
| Water/glycol mixture (15% or more glycol) | 50–99 parts by weight |
| Fatty Alcohol | 1–20 |
| Non-ionic Surfactant | 0–10 |
| Mineral Oil | 0–10 |
| Typical Pharmaceutical Adjuvants | 0–5 |
| Active Ingredients | 0.001–10 |

The fatty alcohol, non-ionic surfactant, and other adjuvants are discussed in U.S. Pat. No. 3,934,013 to Poulsen which is incorporated herein by reference.

The naphthalenes of formula (I) may also be formulated as topical ointments. A "classical" ointment is a semisolid anhydrous composition which may contain mineral oil, white petrolatum, a suitable solvent such as a glycol and may include propylene carbonate and other pharmaceutically suitable additives such as surfactants, for example Span and Tween, or wool fat (lanolin), along with stabilizers such as antioxidants and other adjuvants as mentioned before. Following is an example of a typical "classical" ointment base:

| | | |
|---|---|---|
| White Petrolatum | 40–94 | parts by weight |
| Mineral Oil | 5–20 | |
| Glycol Solvent | 1–15 | |
| Surfactant | 0–10 | |
| Stabilizer | 0–10 | |
| Active Ingredients | 0.001–10.0 | |

Other suitable ointment base formulations which employ propylene carbonate are described in U.S. Pat. No. 4,017,615 issued Apr. 12, 1977 by Shastri et al entitled "Propylene Carbonate Ointment Vehicle" and U.S. Pat. No. 3,924,004 issued Dec. 2, 1975 by Chang et al entitled "Fatty Alcohol-Propylene Carbonate-Glycol Solvent Cream Vehicle". As much of those applications as is pertinent is incorporated herein by reference. Following is a typical ointment base formulation containing propylene carbonate:

| | | |
|---|---|---|
| Active Ingredients | 0.001–10.0 | parts by weight |
| Propylene Carbonate | 1–10 | |
| Solvent | 1–10 | |
| Surfactant | 0–10 | |
| White Petrolatum | 70–97 | |

Suitable solvents, surfactants, stabilizers, etc. are discussed in U.S. Pat. No. 3,934,013 and such are incorporated herein by reference.

A suitable topical "non-classical" anhydrous, water washable "ointment type" base is described in U.S. Pat. No. 3,592,930 to Katz and Neiman, and that patent is incorporated herein by reference. A representative composition of this invention utilizing such base is as follows:

| | | |
|---|---|---|
| Glycol Solvent | 40–35 | parts by weight |

| | |
|---|---|
| Fatty Alcohol | 15-45 |
| Compatible Plasticizer | 0-15 |
| Compatible Coupling Agent | 0-15 |
| Penetrant | 0-20 |
| Active Ingredients | 0.001-10.0 |

Another aspect of the invention is a method for relieving the condition of psoriasis in a mammal by topically administering a composition containing a compound of formula (I) wherein $R^1$, $R^2$, $R^3$ m and n are as defined above. Generally, the anti-psoriatic manifestation in mammals, particularly humans, is combatted by contacting the inflamed areas with a therapeutically effective amount of the naphthalene-containing compositions of this invention, that is, an amount which results in a lessening of the epidermal cell proliferation (an anti-psoriatic effect). Preferably the naphthalenes are first formulated to prepare a suitable pharmaceutical formulation, as discussed hereinabove, which is then placed in contact with the afflicted ares(s). An effective amount of the naphthalene compound will depend upon the particular condition and the mammal receiving the treatment and will vary between 0.001% to 10% by weight of the pharmaceutical composition and preferably will be between 0.01% and 1% by weight of the formulation. Using these levels in the formulation, a therapeutically effective and non-side effect producing amount, i.e. enough to affect an anti-psoriatic response, but not enough to adversely effect the recipient, is applied to the afflicted area(s).

PREPARATION

The compounds of formula (I) may be prepared from compounds of formula (V).

A particularly preferred method of preparing compounds of formula (V) wherein m is not 0 is shown in the following reaction sequence.

REACTION SEQUENCE I

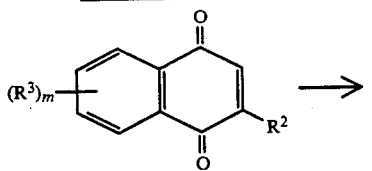 (II)

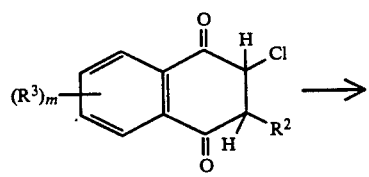 (III)

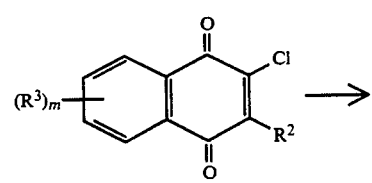 (IV)

-continued
REACTION SEQUENCE I

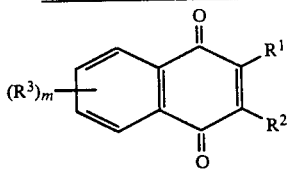 (V)

wherein $R^1$, $R^2$ and $R^3$ are as defined above and m is 1 or 2.

Compounds of formula (II) are prepared according to the method disclosed in J. Am. Chem. Soc., 70, 3165 (1948) and Ibid., 71, 3615 (1949). A substituted butadiene is reacted with 1,4-benzoquinone in a solvent such as acetic acid at a temperature of $-10°$ C. to 30° C., preferably at 25° C. for 24 to 72 hours, preferably from 40 to 48 hours. The 5,8-dihydro compound of formula (II) is recovered and treated with an oxidizing agent. such as sodium dichromate, sodium nitrite and the like as described in the above articles to form compounds of formula (II) wherein $R^2$ is hydrogen. Compounds of formula (II) wherein $R^2$ is alkyl, optionally substituted phenyl or phenylalkyl may be prepared by reacting the naphthoquinone with an acid of the formula $R^2COOH$ wherein $R^2$ is as defined above. A solution of the acid and naphthoquinone in acetonitrile and sulfolane in the presence of a metal nitrate, e.g. silver nitrate and the like, is heated to 50°-100° C., preferably to 55°-75° C. A solution of a persulfate slat, e.g. diammonium persulfate, is added dropwise. Compounds of formula (II) wherein $R^2$ is alkyl, optionally substituted phenyl or phenylalkyl are recovered by conventional means such as chromatrography. Compounds of formula (III) are prepared by bubbling chlorine gas into a solution of compound of formula (II) dissolved in a solvent such as glacial acetic acid, nitrobenzene, carbon tetrachloride and the like, preferably glacial acetic acid at room temperature. This compound, which may be isolated by known means, dissolved in a solvent such as acetic acid is treated with a suitable catalyst such as sodium acetate, iodine, iron-(III) chloride, dimethylformamide or alcohols with heating under reflux for ½ to 4 hours, preferably for 1 to 2½ hours to yield compounds of formula (IV). Compounds of formula (V) are prepared by reacting compound of formula (IV) with an alkali metal alkoxide or phenoxide such as sodium alkoxide or phenoxide, e.g., sodium methoxide or phenoxide in an anhydrous solvent such as methanol, dimethylformamide and the like, the solvent being chosen according to the length of the alkyl chain on the alkoxy group. The reaction mixture is heated under reflux for ½ to 3 hours, preferably for ½ to 1½ hours. Compounds of formula (V) are recovered by conventional means such as by crystallization.

The compounds of formula (V) wherein $R^1$ is alkylthio or phenylthio may be prepared by the method described for the alkoxy or phenoxy compound except that the alkali metal alkoxide or phenoxide is replaced by the alkali metal salt of the alkyl or phenyl mercaptan with the solvent being dimethylformamide and the like.

Compounds of formula (IV) may be converted to compounds of formula (VIII), infra, by treatment with an alcoholic solution of a strong base such as potassium hydroxide in methanol and then alkylating the compound using the appropriate halide or an alcohol as is described hereinafter under Reaction Sequence II.

The butadiene intermediate, such as 2-chloro-1,3-butadiene (chloroprene), 2-methyl-1,3-butadiene(isoprene), 2-ethyl-1,3-butadiene 1-methoxy-1,3-butadiene, 2-phenyl-1,3-butadiene, 1-phenyl-1,3-butadiene and the like are available from, i.a., Pfaltz and Bauer Chemical Co. 2-Bromo-1,3-butadiene and 2-fluoro-1,3-butadiene may be prepared by methods well known in the art, for example, by the methods discussed in J. Am. Chem. Soc., 55 786 (1933) and U.S. Pat. No. 2,401,850, respectively.

Another method for preparing the compounds of formula (V) is depicted in Reaction Sequence II below.

REACTION SEQUENCE II

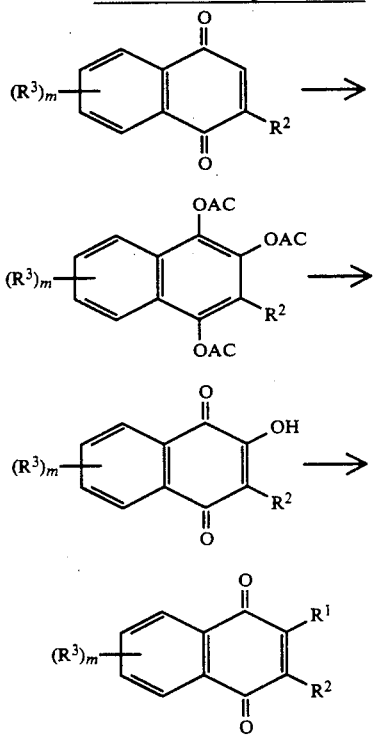

wherein $R^1$, $R^2$, $R^3$ and m are as defined above.

Compound of formula (VI) are commercially available or certain compounds of formula (VI) may be prepared by the method described supra for compounds of formula (II). Compound of formula (VII) is prepared by acylating compound of formula (VI) in the presence of a Lewis acid such as boron trifluoride:etherate and the like. The acylating agent is an acid anhydride such as acetic anhydride, propanoic anhydride and the like, preferably acetic anhydride. Compound of formula (VII) is hydrolyzed by tenement with an alkali metal alkoxide in an alcohol such as sodium methoxide in methanol followed by treatment with aqueous hydrochloric acid to form compound of formula (VIII). Compound of formula (VII) wherein $R^2$ is hydrogen may be converted to the compound wherein $R^2$ is alkyl, optionally substituted phenyl or phenylalkyl by reaction with a peracid anhydride of the formula $(R_2CO_2)_2$ wherein $R^2$ is as defined above. A solution of the unsubstituted compound in a solvent such as glacial acetic acid was heated to 70°–120° C., preferably form 75°–100° C. and an ethereal solution of the anhydride is added dropwise over 1 to 6 hours, preferably over 2 to 4 hours. Compound of formula (VIII) wherein $R^2$ is alkyl, optionally substituted phenyl or phenylalkyl is recovered by precipitation.

Compound of formula (VIII) is converted to compound of formula (V) by reaction with an appropriate halide or an appropriate alcohol.

Compound of formula (VIII) is reacted with an alkyl or aryl halide, e.g. an alkyl bromide or alkyl iodide in a solvent such as tetrahydrofuran and the like. A solution of 1,5-diazobicyclo[5.4.0]undec-5-ene (DBU) in a solvent such as tetrahydrofuran is added dropwise. The precipitate of DBU-hydrogen halide which forms is removed by filtration and the compound of formula (V) is recovered by evaporation.

Compound of formula (V) may also be prepared by reacting compound of formula (VIII) with an alcohol. To a solution of compound of formula (VIII) in the alcohol is added boron trifluoride etherate. The solution is heated form 50° to 100° C., preferably from 60° to 80° C. for ¼ hour to 4 hours, preferably for 1 to 3 hours. Compound of formula (V) is recovered by filtration.

Compounds of formula (I) are prepared from compounds of formula (V) by first hydrogenating to form compounds of formula (IX)

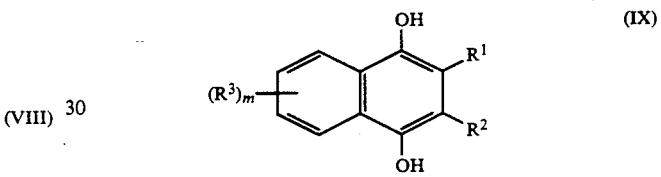

When $R^1$ is alkoxy or phenoxy, compound of formula (V) is hydrogenated in a hydrogen atmosphere and a catalyst such as palladium on charcoal. When $R^1$ is alkylthio or phenylthio or the $R^3$ group contains a sulfur atom, compound of formula (V) is hydrogenated int he presence of cyclohexadiene and a catlayst such as palladium on charcoal. The hydrogenated compound is reacted with an alkanoyl or aroyl anhydride and pyridine/dimethylaminopyridine such as acetic anhydride and the like in a solvent such as tetrahydrofuran, diethyl ether and the like. Compounds of formula (I) are recovered by recrystallization.

The sulfinylnaphthalenes of formula (I) are prepared by oxidation of the corresponding thio compounds with a stoichiometric amount of a suitable peracid in an inert organic solvent.

The compounds of formula (I) bearing a sulfonyl substituent are prepared by further oxidizing the compounds of formula (I) wherein $R^3$ is a sulfinyl group with a suitable peracid typically at $-10°$ to 75° C. for 1 to 10 hours. Preferably, m-chloroperbenzoic acid in an inert organic solvent at room temperature is used to prepare the desired sulfonyl compounds.

The acid anhydrides are commercially available from, i.a., Aldrich Chemical Co. or if not available may be prepared by condensing the appropriate acid in the presence of acetic anhydride or acetyl chloride containing a trace of phosphoric acid.

The following specific description is given to enable those skilled in the art to more clearly understand and practice the present invention. It should not be considered as a limitation upon the scope of the invention but merely as illustrative and representative thereof.

PREPARATION I

A solution of 1,4-naphthoquinone (7.91 g), propanoic acid (3.70 g) and silver nitrate (1.53 g) in a mixture of acetonitrile (11.4 mL), sulfolane (34.1 mL) and water (79.5 mL) was heated at 60°–65° C. for 2 hours. A solution of ammonium persulfate (13.7 g) in water (25 mL) was then added dropwise. The mixture was cooled in ice water and extracted with ether. The organic layer was washed with saturated sodium bicarbonate, water and brine, then dried, filtered and evaporated. Chromatography over silica gel afforded 2-ethyl-1,4-naphthoquinone, m.p. 87°–88° C.

Similarly, using the above procedure, the following compounds may be prepared:
2-methyl-1,4-naphthoquinone;
6-chloro-2-methyl-1,4-naphthoquinone;
6-chloro-2-n-propyl-,4-naphthoquinone;
6-methoxy-2-ethyl-1,4-naphthoquinone;
5-cyano-2-methyl-1,4-naphthoquinone;
2-phenyl-1,4-naphthoquinone;
2,6,7-trimethyl-1,4-naphthoquinone; and
6-methylthio-2-n-propyl-1,4-naphthoquinone.

PREPARATION II a) Chlorine was bubbled through a solution of 1,4-naphthoquinone (39.5 g) in glacial acetic acid maintained at 15° C. by cooling. The precipitated intermediate dichloride was isolated by filtration and then suspended in fresh glacial acetic acid (500 mL). Anhydrous sodium acetate (25 g) was added, and the mixture was brought to reflux. Water was then added, and the mixture was allowed to cool, precipitating 2-chloro-1,4-naphthoquinone, collected by filtration and air drying, m.p. 118° C.

b) 2-Chloro-3-methyl-1,4-naphthoquinone was prepared analogously, except that the intermediate dichloride was isolated as an oil after evaporation, aqueous extraction with either and evaporation. Conversion of this intermediate using sodium acetate in acetic acid gave 2-chloro-3-methyl-1,4-naphthoquinone, m.p. 155°–156° C.

Similarly, using the above procedure, the following compounds are prepared:
2,6-dichloro-1,4-naphthoquinone;
2,5-dichloro-1,4-naphthoquinone;
2-chloro-6-methoxy-1,4-naphthoquinone;
2-chloro-6-ethoxy-1,4-naphthoquinone;
2-chloro-6-i-butoxy-1,4-naphthoquinone;
2-chloro-6-phenylethoxy-1,4-naphthoquinone;
2-chloro-5-cyano-1,4-naphthoquinone;
2-chloro-6-cyano-1,4-naphthoquinone;
2-chloro-6-(2-chlorophenylthio)-1,4-naphthoquinone;
2-chloro-5(3-chlorophenylthio)-1,4-naphthoquinone;
2-chloro-3-phenyl-1,4-naphthoquinone;
2-chloro-6-(4-chlorophenylthio)-1,4-naphthoquinone;
2-chloro-5-(2,6-dichlorophenylthio)-1,4-naphthoquinone;
2-chloro-5-(4-fluorophenylthio)-1,4naphthoquinone;
2-chloro-5-(2-bromophenylthio)-1,4-naphthoquinone;
2-chloro-6-(4-bromophenylthio)-1,4-naphthoquinone;
2-chloro-6-(4-methoxyphenylthio)-1,4-naphthoquinone;
2-n-chloro-6-(4-nitrophenylthio)-1,4-naphthoquinone;
2-n-chloro-6-(2ethylphenylthio)-1,4-naphthoquinone;
2-n-chloro-6-pyridin-2-ylthio-1,4-naphthoquinone;
2-n-chloro-6-pyridin-4-ylthio-1,4-naphthoquinone;
2-chloro-6-bromo-1,4-naphthoquinone;
2-chloro-6-fluoro-1,4-naphthoquinone;
2-chloro-6-methyl-1,4-naphthoquinone;
2-chloro-6-i-propyl-1,4-naphthoquinone;
2-chloro-6-phenyl-1,4-naphthoquinone;
2-chloro-6-benzyl-1,4-naphthoquinone;
2-chloro-6,7-dimethyl-1,4-naphthoquinone;
2-chloro-5-methoxy-1,4-naphthoquinone;
2-chloro-5-phenyl-1,4-naphthoquinone;
2,7-dichloro-1,4-naphthoquinone;
2-chloro-7-methyl-1,4-naphthoquinone;
2-chloro-3-ethyl-1,4-naphthoquinone;
2chloro-3-methyl-1,4-naphthoquinone;
2,6-dichloro-3-methyl-1,4-naphthoquinone;
2-chloro-3-ethyl-6-methoxy-1,4-naphthoquinone;
2-chloro-5-cyano-3-methyl-1,4-naphthoquinone;
2-chloro-3,6,7-trimethyl-1,4-naphthoquinone;
2-chloro-6-methylthio-3-n-propyl-1,4-naphthoquinone; and
2,6-dichloro-3-n-propyl-1,4-naphthoquinone;

PREPARATION III

A solution of 2-chloro-3-methyl-1,4-naphthoquinone (10.3 g) in tetrahydrofuran (100 mL) was treated dropwise with a solution of sodium methoxide (320 g) in tetrahydrofuran (25 mL) at room temperature. After stirring overnight, the mixture was evaporated, and the residue was taken up in ether. The organic layer was washed with brine, dried, filtered and evaporated. Chromatography over silica gel gave 2-methoxy-3methyl-1,4-naphthoquinone, m.p. 93°–94° C.

Similarly, using the above procedure, the following compounds are prepared;
6-chloro-2-methoxy-1,4-naphthoquinone;
5-chloro-2-ethoxy-1,4-naphthoquinone;
6-chloro-2-ethoxy-1,4-naphthoquinone;
5-chloro-2-n-propoxy-1,4-naphthoquinone;
6-chloro-2-n-propoxy-1,4-naphthoquinone;
5-chloro-2-i-propoxy-1,4-naphthoquinone;
6-chloro-2-i-propoxy-1,4-naphthoquinone;
5-chloro-2-n-butoxy-1,4-naphthoquinone;
6-chloro-2-n-butoxy-1,4-naphthoquinone;
5-chloro-2-s-butoxy-1,4-naphthoquinone;
6-chloro-2-s-butoxy-1,4-naphthoquinone;
5-chloro-2-n-pentyloxy-1,4-naphthoquinone;
6-chloro-2-n-pentyloxy-1,4-naphthoquinone;
5-chloro-2-s-pentyloxy-1,4-naphthoquinone;
6-chloro-2-s-pentyloxy-1,4-naphthoquinone;
5-chloro-2-n-hexyloxy-1,4-naphthoquinone;
6-chloro-2-n-hexyloxy-1,4-naphthoquinone;
5-chloro-2-i-hexyloxy-1,4-naphthoquinone;
6-chloro-2-i-hexyloxy-1,4-naphthoquinone;
5-chloro-2-(2,2-dimethylpropoxy)-1,4-naphthoquinone;
6-chloro-2-(2,2-dimethylpropoxy)-1,4-naphthoquinone;
6-methoxy-2-methoxy-1,4-naphthoquinone;
6-ethoxy-2-ethoxy-1,4-naphthoquinone;
6-i-butoxy-2-methoxy-1,4-naphthoquinone;
6-phenylethoxy-2-methoxy-1,4-naphthoquinone;
6-chloro-2-methylthio-1,4-naphthoquinone;
6-chloro-2-i-propylthio-1,4-naphthoquinone;
6-chloro-2-n-hexylthio-1,4-naphthoquinone;
5-cyano-2-methoxy-1,4-naphthoquinone;
6-cyano-2-methoxy-1,4-naphthoquinone;
2-methoxy-6-(2-chlorophenylthio)-1,4-naphthoquinone;
2-methoxy-5-(3-chlorophenylthio)-1,4-naphthoquinone;
2-methoxy-6-(4-chlorophenylthio)-1,4-naphthoquinone;
2-methoxy-5-(2,6-dichlorophenylthio)-1,4-naphthoquinone;
2-methoxy-5-(4-fluorophenylthio)-1,4-naphthoquinone;
2-methoxy-5-(2-bromophenylthio)-1,4-naphthoquinone;

2-methoxy-6-(4-bromophenylthio)-1,4-naphthoquinone;
2-ethoxy-6-(4-methoxyphenylthio)-1,4-naphthoquinone;
2-n-propoxy-6-(4-nitrophenylthio)-1,4-naphthoquinone;
2-n-butoxy-6-(2-ethylphenylthio)-1,4-naphthoquinone;
2-n-pentyloxy-6-pyridin-2-ylthio-1,4-naphthoquinone;
2-n-hexyloxy-6-pyridin-4-ylthio-1,4-naphthoquinone;
2-methoxy-5-(4-acetylaminophenylthio)-1,4-naphthoquinone;
2-methoxy-6-methylthio-1,4-naphthoquinone;
2-methoxy-5-benzylthio-1,4-naphthoquinone;
2-methoxy-6-ethylthio-1,4-naphthoquinone;
2-methoxy-5-methoxycarbonylmethylthio-1,4-naphthoquinone;
6-bromo-2-methoxy-1,4-naphthoquinone;
6-fluoro-2-methoxy-1,4-naphthoquinone;
6-methyl-2-methoxy-1,4-naphthoquinone;
6-i-propyl-2-methoxy-1,4-naphthoquinone;
6-phenyl-2-methoxy-1,4-naphthoquinone;
6-benzyl-2-methoxy-1,4-naphthoquinone;
6-chloro-2-phenoxy-1,4-naphthoquinone;
6-chloro-2-(4-chlorophenoxy)-1,4-naphthoquinone;
6-chloro-2-phenylthio-1,4-naphthoquinone;
6-methoxy-2-phenoxy-3-ethyl-1,4-naphthoquinone;
5-cyano-2-methoxy-3-methyl-1,4-naphthoquinone;
3,6,7-timethyl-2-ethoxy-3-methyl-1,4-naphthoquinone;
6-methylthio-2-phenylthio-3-n-propyl-1,4-naphthoquinone;
2-methoxy-3-phenyl-1,4-naphthoquinone;

PREPARATION IV

A solution of 10% aqueous potassium hydroxide (150 mL) was added to a solution of 2-chloro-3-methyl-1,4-naphthoquinone (10.3 g) in refluxing methanol (500 mL). After cooling and acidification with concentrated hydrochloric acid, the precipitated product was collected by filtration to give 2-hydroxy-3-methyl-1,4-naphthoquinone, m.p. 173°–174° C.

Similarly, using the above procedure, the following compounds are prepared:
2-hyroxy-1,4-naphthoquinone;
6-chloro-2-hydroxy-1,4-naphthoquinone;
6,7-dimethyl-2-hydroxy-1,4-naphthoquinone;
6-chloro-2-hydroxy-3-methyl-1,4-naphthoquinone; and
6-methyl-2-hydroxy-3-ethyl-1,4-naphthoquinone.

PREPARATION V

A solution of 1,4-naphthoquinone (79 g) in acetic anhydride (200 mL) and boron trifluoride etherate (10 mL) was heated overnight, then cooled to room temperature to give 1,2,4-triacetyloxynaphthalene, m.p. 136°–137° C.

Similarly, using the above procedure, the following compounds are prepared:
1,2,4-triacetyloxy-3-methylnaphthalene;
6- and 7- chloro-1,2,4-triacetyloxynaphthalene, m.p. 132°–135° C., as a mixture of isomers;
1,2,4-triacetyloxy-3-ethylnaphthalene;
1,2,4-triacetyloxy-6-cyanonaphthalene;
1,2,4-triacetyloxy-6,7-dimethylnaphthalene; and
1,2,4-triacetyloxy-6-methylthionaphthalene.

PREPARATION VI 1,2,4-Triacetoxynaphthalene (75.5 g) was added to a clear solution of sodium methoxide (from 26.6 g Na) in methanol (625 mL). After 1 hour, the resulting red paste was collected by filtration, then dissolved in water and acidified with concentrated hydrochloric acid. The yellow precipitate was collected, recrystallized from acetic acid to give 2-hydroxy-1,4-naphthoquinone, m.p. 195° C.

Similarly, using the above procedure, the following compounds are prepared:
2-hydroxy-3-methyl-1,4-naphthoquinone, m.p. 174° C.;
2-hydroxy-3-ethyl-1,4-naphthoquinone;
2-hydroxy-6,7-dimethyl-1,4-naphthoquinone; and
2-hydroxy-6-methyl-1,4-naphthoquinone.

PREPARATION VII

A solution of 2-hydroxy-1,4-naphthoquinone (17.4 g) in glacial acetic acid heated to 95° C. (oil bath) was treated dropwise with an ethereal solution of acetyl peroxide over 3 hours. When gas evolution ceased, the mixture was cooled and reduced in volume by evaporation. Addition of water precipitated 2-hydroxy-3-methyl-1,4-naphthoquinone, m.p. 172°–173° C.

Similarly, using the above procedure, the following compounds are prepared:
6-chloro-2-hydroxy-3-methyl-1,4-naphthoquinone;
6-chloro-2-hydroxy-3-ethyl-1,4-naphthoquinone;
2-hydroxy-3-n-propyl-1,4-naphthoquinone:
6-methyl-2-hydroxy-3-n-butyl-1,4-naphthoquinone; and
6,7-dimethyl-2-hydroxy-3-ethyl-1,4-naphthoquinone.

PREPARATION VIII

A solution of 2-hyroxy-3-methyl-1,4-naphthoquinone (18.8 g) and methyl iodide (7.5 mL) in tetrahydrofuran (250 mL) is treated dropwise with a solution of DBU (16.4 mL) in tetrahydrofuran (50 mL). The resulting precipitate of DBU.HI is removed by filtration, and the filtrate is evaporated. Recrystallization from methanol gave 2-methoxy-3-1,4-napththoquinone, m.p. 94° C.

Similarly, using the above procedure, the following compounds are prepared:
2-ethoxy-3-methyl-1,4-napththoquinone;
6-chloro-2-methoxy-3-methyl-1,4-napththoquinone;
6-chloro-2-ethoxy-1,4-napththoquinone;
2-n-propoxy-3-n-propyl-1,4-napththoquinone;
6-methyl-2-methoxy-3-n-butyl-1,4-napththoquinone;
6,7-dimethyl-2-i-propoxy-1,4-napththoquinone;
2-i-butoxy-1,4-napththoquinone;
2-n-butoxy-1,4-napththoquinone;
2-i-propxy-1,4-napththoquinone;
2-n-dodecyloxy-1,4-napththoquinone;
2-phenoxy-1,4-napththoquinone;
2-ethoxy-1,4-napththoquinone;
2-n-propoxy-1,4-napththoquinone;
6-chloro-2-ethoxy-3-ethyl-1,4-napththoquinone;
2phenoxy-3-ethyl-1,4-napththoquinone;
6,7-dimethyl-2-methoxy-1,4-napththoquinone;
6-methyl-2-(4-methylhenoxy)-1,4-napththoquinone;
2-methoxy-3-n-propyl-1,4-napththoquinone;
6-methyl-2-n-butoxy-3-n-butyl-1,4-napththoquinone;
6,7-dimethyl-2-methoxy-3-ethyl-1,4-napththoquinone; and
2-phenoxy-3-ethyl-1,4-napththoquinone;

PREPARATION IX

A solution of 2-hydroxynaphthoquinone (10.44 g) in methanol (200 mL) and boron trifluoride etherate (20 mL) was heated at 70° C. for 2 hours. After cooling, the resulting precipitate was collected by filtration to yield 2-methoxy-1,4-napththoquinone, m.p. 183° C.

Similarly, using the above procedure, the following compounds are prepared:
6-chloro-2-methoxy-1,4-napththoquinone;

6-chloro-2-ethoxy-1,4-napththoquinone;
2-methoxy-3-methoxy-1,4-napththoquinone; and
6,7-dimethyl-2-n-propoxy-1,4-napththoquinone.

PREPARATION X

2-Dimethoxy-5-(4-methylpyridiniumthio)-1,4-napththoquinone methyl sulfate.

A mixture of dimethylsulfate (0.19 ml, 2 mmol) and 2-methoxy-5-(4-methylpyridinylthio)-1,4-napththoquinone (327 mg, 1 mmol) in tetrahydrofuran (10 ml) was heated under reflux for 3 hours and then cooled to 20° C. The orange solid was filtered off, washed with tetrahydrofuran and recrystallized from ethanol:isopropanol giving 279 mg of 2-methoxy-5-(4-methylpyridiniumthio) -1,4-napththoquinone methyl sulfate mp 160°-162° C. and a second crop of 110 mg.

Similarly prepared is 2-methoxy-5-(2-methylpyridiniumthio) -1,4-napththoquinone methyl sulfate.

Similarly, the following compounds are prepared by the above method:
2-methoxy-5-(2-methylpyridiniumsulfinyl)-1,4-napththoquinone methyl sulfate; and
2-methoxy-5-(4-methylpyridiniumsulfinyl)-1,4-napththoquinone methyl sulfate.

EXAMPLE 1

A solution of 2-methoxy-1,4-napththoquinone (15.0 g, 80 mmol) in tetrahydrofuran (1 L) was hydrogenated at atmospheric pressure over 10% palladium on carbon (1.5 g). When the solution had gone colorless, a solution of propanoic anhydride (41.6 g) pyridine (25 g) and dimethylaminopyridine (1.0 g) in tetrahydrofuran (100 mL) was added. The mixture was stirred overnight, then filtered to remove catalyst, and evaporated. The residue was dissolved in ether, and was washed with 1 M hydrochloric acid and with brine, dried, filtered and evaporated. Crystallization from ether-petroleum ether gave 2-methoxy-1,4-dipropropanyloxynaphthalene, m.p. 92°-93° C.

Similarly, using the above procedure substituting the appropriate compound of formula (V) for 2-methoxy-1,4-napththoquinone, where appropriate, and the appropriate acid anhydride for propanoic anhydride, where appropriate, the following compounds are prepared:
6- and 7- chloro-2-methoxy-1,4-diacetyloxynaphthalene, m.p. 77°-78° C.;
2-isobutoxy-1,4-diacetyloxynaphthalene;
2-n-butoxy-1,4-diacetyloxynaphthalene;
2-isopropoxy-1,4-diacetyloxynaphthalene, m.p. 69°-70° C.;
2-n-dodecyloxy-1,4-diacetyloxynaphthalene, m.p. 61°-62° C.;
2-phenoxy-1,4-diacetyloxynaphthalene;
2-methoxy-1,4-diacetyloxynaphthalene, m.p. 137°-138° C.;
2-methoxy-1,4-di(2,2-dimethylpropanoyloxy)naphthalene; m.p. 109°-110° C.;
2-methoxy-1,4-di-i-butanoyloxynaphthalene, m.p. 79°-80° C.;
2-methoxy-1,4-di-n-butanoyloxynaphthalene, m.p. 68° C.;
2-methoxy-1,4-dibenzoyloxynaphthalene;
2-ethoxy-1,4-diacetyloxynaphthalene, m.p. 64°-65° C.;
2-ethoxy-1,4-dipropanoyloxynaphthalene, m.p. 64°-64° C.;
2-ethoxy-1,4-di-i-butanoyloxynaphthalene;
2-ethoxy-1,4-di(2,2-dimethylpropanoyloxy)naphthalene, m.p. 78°-79° C.;
2-ethoxy-1,4-dibenzoyloxynaphthalene, m.p. 172°-173° C.;
2-propoxy-1,4-diacetyloxynaphthalene;
2-propoxy-1,4-dipropanoyloxynaphthalene;
6-chloro-2-methoxy-1,4-di-n-propanoyloxynaphthalene;
6-chloro-2-methoxy-1,4-di-i-butanoyloxynaphthalene;
6-chloro-2-methoxy-1,4-di(2,2-dimethylpropanoyloxy)naphthalene;
6-chloro-2-methoxy-1,4di-n-octanoyloxynaphthalene;
6-chloro-2-n-butoxy-1,4-diacetyloxynaphthalene;
6-chloro-2-s-butoxy-1,4-diacetyloxynaphthalene;
6-chloro-2-(2,2-dimethylpropoxy)-1,4-diacetyloxynaphthalene;
2-n-butoxy-1,4-di-n-pentoyloxynaphthalene;
6-chloro-2-n-propoxy-1,4-dipropanoyloxynaphthalene;
6-chloro-2-i-propoxy-1,4-dioctanoyloxynaphthalene;
6-chloro-2-methoxy-1,4-diacetyloxynaphthalene;
6-fluoro-2-methoxy-1,4-diacetyloxynaphthalene;
5-chloro-2-methoxy-1,4-diacetyloxynaphthalene;
5-cyano-2-methoxy-1,4-diacetyloxynaphthalene;
6-cyano-2-methoxy-1,4-diacetyloxynaphthalene;
6-methylamino-2-methoxy-1,4-diacetyloxynaphthalene;
6-diethylamino-2-methoxy-1,4-dipropanoyloxynaphthalene;
6-ethylmethylamino-2-methoxy-1,4-di-n-butanoyloxynaphthalene;
6-methoxy-2-methoxy-1,4-di-n-pentanoyloxynaphthalene;
6-ethoxy-2-ethoxy-1,4-di-n-hexanoyloxynaphthalene;
6-i-butoxy-2-methoxy-1,4-di-n-hexanoyloxynaphthalene;
6-i-butoxy-2-1,4-di(2,2-dimethylpropanoyloxy)naphthalene;
6-phenylethoxy-2-methoxy-1,4-diacetyloxynaphthalene;
6-methoxy-2-methoxy-1,4-diacetyloxynaphthalene;
6-i-propyl-2-methoxy-1,4-diacetyloxynaphthalene;
6-phenyl-2-methoxy-1,4-diacetyloxynaphthalene;
6-benzyl-2-methoxy-1,4-diacetyloxynaphthalene;
5-chloro-2-n-pentyloxy-1,4-diacetyloxynaphthalene;
5-chloro-2-s-pentyloxy-1,4-diacetyloxynaphthalene;
5-chloro-2-n-hexyloxy-1,4-diacetyloxynaphthalene;
5-chloro-2-i-hexyloxy-1,4-diacetyloxynaphthalene;
6-chloro-2-phenoxy-1,4-diacetyloxynaphthalene;
6-chloro-2(4-chlorophenoxy)-1,4-diacetyloxynaphthalene;
6-methoxy-2-phenoxy-3-ethyl-1,4-diacetyloxynaphthalene;
5-cyano-2-methoxy-3-methyl-1,4-diacetyloxynaphthalene;
3,6,7-trimethyl-2-ethoxy-1,4-di-i-propanoyloxynaphthalene;
2-phenoxy-3-ethyl-1,4-diacetyloxynaphthalene;
6,7-dimethyl-2-methoxy-1,4-diacetyloxynaphthalene;
6-methyl-2-(4-methylphenoxy)-1,4-diacetyloxynaphthalene;
6-methyl-2-(4-methylphenoxy)1,4-di-n-butanoyloxynapthelene;
6-methyl-2-n-butoxy-3-n-butyl-1,4-diacetyloxynaphthalene;
6,7-dimethyl-2-methoxy-3-ethyl1,4-di-i-butanoyloxynaphthalene;
2-phenoxy-3-ethyl-1,4-diacetyloxynaphthalene;
2-ethoxy-3-1,4-diacetyloxynaphthalene;
2-ethoxy-3-methyl-1,4-di-n-pentanoyloxynaphthalene;

6-chloro-2-methoxy-3-methyl-1,4-di-n-propanoyloxynaphthalene;
6-chloro-2-methoxy-3-methyl-1,4-di-(2,2-dimethylpropanoyloxy)naphthalene;
2-n-propoxy-3-n-propyl-1,4-di-n-octanoyloxynaphthalene;
6,7-dimethyl-2-i-propoxy-1,4-di-acetyloxynaphthalene;
6,7-dimethyl-2-n-propoxy-1,4-di-acetyloxynaphthalene;
6-chloro-2-phenoxy-1,4-dibenzoyloxynaphthalene;
6-chloro-2-(4-chlorophenoxy)-1,4-di-phenylacetyloxynaphthalene;
5-cyano-2-methoxy-3-methyl-1,4-di-(2-chlorobenzoyloxy)naphthalene;
6-chloro-2-ethoxy-3-ethyl-1,4-di-benzxoyloxynaphthalene;
6-chloro-2-ethoxy-3-ethyl-1,4-di-benzoyloxynaphthalene;
6-chloro-2-ethoxy-3-ethyl-1,4-di-phenylacetyloxynaphthalene;
6,7-dimethyl-2-methoxy-3-ethyl-1,4-di-(4-methylbenzoyloxy)naphthalene;
2-phenoxy-3-ethyl-1,4-dibenzyoyloxynaphthalene;
2-methoxy-3-methyl-1,4-dibenzxoyloxynaphthalene;
2-methoxy-3-methyl-1,4-dipehnylacetyloxynaphthalene;
2-ethoxy-3-methyl-1,4-dibenzoyloxy-naphthalene;
6-chloro-2-methoxy-3-methyl-1,4di(4-methoxyphenylacetyloxy)naphthalene;
6-methyl-2-methoxy-3-n-butyl-1,4-di-benzoyloxynaphthalene;
6-methyl-2-i-propoxy-3-i-butyl-1,4-di-phenylacetyloxynaphthalene;
2-methoxy-3-phenyl-1,4-diacetyloxynaphthalene; and
2-methoxy-3-phenyl-1,4-dibenzoyloxynaphthalene.

EXAMPLE 2

A solution of 2-phenylthio-3-methyl-1,4-naphthoquinone (28.0 g) and 10% palladium on charcoal (56 g) in tetrahydrofuran (1 L) was treated with 1,4-cyclohexadiene (80 mL), stirred overnight at room temperature. The mixture was then treated with a solution of acetic anhydride (40 mL), pyridine (40 mL) and dimethylaminopyridine (2.0 g) in tetrahydrofuran (100 mL), and stirred for 1 hour. Filtration to remove catalyst, followed by aqueous extraction workup as in Example 1, gave 2-phenylthio-3-methyl-1,4-diacetoxynaphthalene.

Similarly proceeding as above, substituting the appropriate compound for 2-phenylthio-3-methyl-1,4-naphthoquinone and the appropriate acid anhydride, where appropriate, for acetic anhydride, the following compounds, for example, are prepared:
6-chloro-2-methylthio-1,4-diacetyloxynaphthalene;
6-chloro-2-i-propylthio-1,4-diacetyloxynaphthalene;
6-chloro-2-n-hexylthio-1,4-diacetyloxynaphthalene;
2-methoxy-6-(2-chlorophenylthio)-1,4-diacetyloxynaphthalene;
2-methoxy-5-(3-chlorophenylthio)-1,4-diacetyloxynaphthalene;
2-methoxy-6-(4-chlorophenylthio)-1,4-diacetyloxynaphthalene;
2-methoxy-5-(2,6-dichlorophenylthio)-1,4-diacetyloxynaphthalene;
2-methoxy-5-(4fluorophenylthio)-1,4-diacetyloxynaphthalene;
2-methoxy-5-(2-bromophenylthio)-1,4-diacetyloxynaphthalene;
2-methoxy-6-(4-bromophenylthio)-1,4-diacetyloxynaphthalene;
2-ethoxy-6-(4-methoxyphenylthio)-1,4-diacetyloxynaphthalene;
2-n-propoxy-6-(4-nitrophenylthio)-1,4-diacetyloxynaphthalene;
2-n-butoxy-6-(2-ethylphenylthio)-1,4-diacetyloxynaphthalene;
2-n-pentyloxy-6-pyridin-2-ylthio-1,4-diacetyloxynaphthalene;
2-n-hexyloxy-6-pyridin-4-ylthio-1,4-diacetyloxynaphthalene;
2-methoxy-5-(4-acetylaminophenylthio)-1,4-diacetyloxynaphthalene;
6-chloro-2phenylthio-1,4-diacetyloxynaphthalene;
6-chloro-2-phenylthio-1,4-dibenzoyloxynaphthalene;
6-chloro-2-phenylthio-1,4-diphenylacetyloxynaphthalene;
6-methylthio-2-phenylthio-3-n-propyl-1,4-diacetyloxynaphthalene; and
6-methylthio-2-phenylthio-3-n-propyl-1,4-dibenzoyloxynaphthalene.

EXAMPLE 3

(Preparation of Compounds of Formula (I) where $R^3$ is phenylsulfinyl).

Forty percent (w/v) peracetic acid in acetic acid (1 ml) is added over 3-0 minutes to a solution of 2,-methoxy-5-phenylthio-1,4-diacetyloxynaphthalene (0.98 g, 3 mmol) in methylene chloride (15 ml). Excess peracetic acid is destroyed by the addition of a few milligrams of 5% palladium on carbon and the mixture filtered through a celite bed. The filtrate is concentrated in vacuo nd the residue recrystallized from methanol giving 0.59 g of 2-methoxy-5-phenylsulfinyl-1,4diacetyloxynaphthalene.

Similarly, using either peracetic acid or m-chloroperbenzoic acid, the following compounds ar prepared from the respective thio compounds:
2-methoxy-5-(imidazol-2-ylsulfinyl)1,4-diacetyloxynaphthalene;
2-methoxy-6-(2-chlorophenylsulfinyl)-1,4-diacetyloxynaphthalene;
2-methoxy-5-(3-chlorophenylsulfinyl)-1,4-diacetyloxynaphthalene;
2-methoxy-6-(4-chlorophenylsulfinyl)-1,4-diacetyloxynaphthalene;
2-methoxy-5-(2,6-dichlorophenylsulfinyl)-1,4-diacetyloxynaphthalene;
2-methoxy-5-(4-fluorophenylsulfinyl)-1,4-diacetyloxynaphthalene;
2-methoxy-5-(2-bromophenylsulfinyl)-1,4-diacetyloxynaphthalene;
2-methoxy-5-(4-bromophenylsulfinyl)-1,4-diacetyloxynaphthalene;
2-ethoxy-6-(4-methoxyphenylsulfinyl)-1,4-diacetyloxynaphthalene;
2-propoxy-6-(4-nitrophenylsulfinyl)-1,4-diacetyloxynaphthalene;
2-n-butoxy-6-(2-ethylphenylsulfinyl)-1,4-diacetyloxynaphthalene;
2-methoxy-6-(pyrimidin-2-ylsulfinyl)-1,4-diacetyloxynaphthalene;
2-methoxy-5-(pyrimidin-4-ylsulfinyl)-1,4-diacetyloxynaphthalene;
2-methoxy-6-methylsulfinyl-1,4-diacetyloxynaphthalene;

2-methoxy-5-benzylsulfinyl-1,4-diacetyloxynaphthalene; and 2-methoxy-5-methoxycarbonylmethylsulfinyl-1,4-diacetyloxynaphthalene.

EXAMPLE 4

2-methoxy-5-phenylsulfonyl-1,4-diacetyloxynaphthalene (Preparation of Compound of Formula (I) where R³ is phenylsulfonyl).

A mixture of m-chloroperbenzoic acid (300 mg) and 2-methoxy-5-phenylthio-1,4-naphthoquinone (200 mg, 0.61 mmol) in methylene chloride (5 ml) is stirred at 22° C. for 16 hours and the resulting solution then passed through an alumina column (10 g of Activity 1) eluting with chloroform. The eluates are concentrated to dryness and the residue is crystallized from isopropanol giving 95 mg of 2-methoxy-5-phenylsulfonyl-1,4-diacetyloxynaphthalene.

What is claimed is:

1. A composition in a form suitable for topical administration for treating the condition of psoriasis which composition comprises a pharmaceutically acceptable, non-toxic carrier and a psoriasis relieving amount of a compound of the formula:

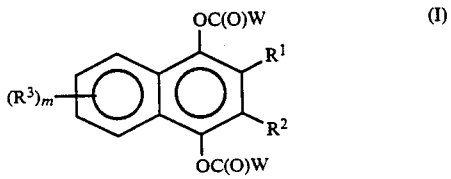

wherein:

m is 0, 1 or 2;

$R^1$ is alkoxy of one to twelve carbon atoms, alkylthio of one to twelve carbon atoms, phenoxy or phenylthio optionally substituted by one or two lower alkyl of one to four carbon atoms, lower alkoxy of one to four carbon atoms or halo;

$R^2$ is hydrogen, lower alkyl of one to six carbon atoms, phenyl or phenylalkyl wherein the phenyl ring of the phenylalkyl group is optionally substituted by one or two substituents selected from the group consisting of halo, lower alkyl of one to four carbon atoms or lower alkoxy of one to four carbon atoms;

$R^3$ is halo, lower alkyl, lower alkoxy, optionally substituted phenyl, optionally substituted phenyl lower alkyl, optionally substituted phenyl lower alkoxy, amino, lower alkylamino, lower dialkylamino, cyano, or $S(O)_nR$ wherein n is 0, 1 or 2, and R is lower alkyl of on to six carbon atoms, optionally substituted phenyl, optionally substituted phenyl lower alkyl, or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano;

W is alkyl of one to seven carbon atoms, phenyl or benzyl optionally substituted with one or two lower alkyl of one to four carbon atoms, lower alkoxy of one to four carbon atoms or halo;

with the proviso that (a) is $R^1$ is methoxy or ethoxy, $R^2$ is hydrogen an W is methyl; or if $R^1$ is methoxy, $R^2$ is methyl and W is methyl, then m is not 0; or (b) if $R^3$ is phenyl, phenyl lower alkyl, phenyl lower alkoxy, amino, lower alkylamino, lower dialkylamino, cyano, or $S(O)_nR$, then m is not 2;

or a pharmaceutically acceptable acid addition salt thereof.

2. The composition of claim 1, wherein m is 2.

3. The composition according to claim 1 whrien the compound is

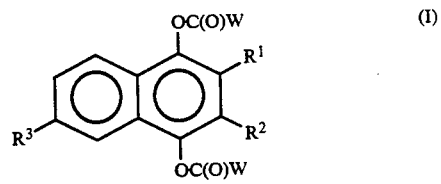

wherein $R^1$, $R^2$, $R^3$, and W are as defined in claim 1.

4. The composition of claim 3 wherein W is alkyl of one to seven carbon atoms.

5. The composition of claim 4 wherein $R^1$ is alkoxy of one to twelve carbon atoms or alkylthio of one to twelve carbon atoms.

6. The composition of claim 5 wherein $R^2$ is hydrogen.

7. The composition of claim 5 wherein $R^2$ is lower alkyl of one to six carbon atoms, phenyl or phenylalkyl optionally substituted by one or two lower alkyl of one to four carbon toms, lower alkoxy of one to four carbon atoms or halo.

8. The composition of claim 4 wherein $R^1$ is phenoxy or phenylthio optionally substituted by one or two lower alkyl of one to four carbon atoms, lower alkoxy of one to four carbon atoms or halo.

9. The composition of claim 8 wherein $R^2$ is hydrogen.

10. The composition of claim 8 wherein $R^2$ is lower alkyl of one to six carbon atoms, penyl or phenylalkyl optionally substituted by one or two lower alkyl of one to four carbon atoms, lower alkoxy of one to four carbon atoms or halo.

11. The composition of claim 3 wherein W is phenyl or benzyl optionally substituted by one or two lower alkyl of one to four carbon atoms, lower alkoxy of one to four carbon atoms or halo.

12. The composition of claim 11 wherein $R^1$ is alkoxy of one to twelve carbon atoms or alkylthio of one to twelve carbon atoms.

13. The composition of claim 12 wherein $R^2$ is hydrogen.

14. The composition of claim 12 wherein $R^2$ is lower alkyl of one to six carbon atoms, phenyl or phenylalkyl optionally substituted by one or two lower alkyl of one to four carbon atoms, lower alkoxy of one to four carbon atoms or halo.

15. The composition of claim 11 wherein $R^1$ is phenoxy or phenylthio optionally substituted by one or two lower alkyl of one to four carbon atoms, lower alkoxy of one to four carbon atoms or halo.

16. The composition of claim 15 wherein $R^2$ is hydrogen.

17. The composition of claim 15 wherein $R^2$ is lower alkyl of one to six carbon atoms, phenyl or phenylalkyl optionally substituted by one or two lower alkyl of one to four carbon atoms, lower alkoxy of one to four carbon atoms or halo.

18. A method of treating psoriasis in mammals which comprises applying an effective amount of a compound of the formula:

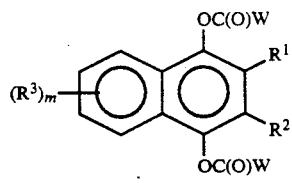

wherein:
m is 0, 1 or 2;
R¹ is alkoxy of one to twelve carbon atoms, alkylthio of one to twelve carbon atoms, phenoxy or phenylthio optionally substituted by one or two lower alkyl of one to four carbon atoms, lower alkoxy of one to four carbon atoms or halo;
R² is hydrogen, lower alkyl of one to six carbon atoms, phenyl or phenylalkyl wherein the phenyl ring of the phenylalkyl group is optionally substituted by one or two substituents selected from the group consisting of halo, lower alkyl of one to four carbon atoms or lower alkoxy of one to four carbon atoms;
R³ is halo, lower alkyl, lower alkoxy, optionally substituted phenyl, optionally substituted phenyl lower alkyl, optionally substituted phenyl lower alkoxy, amino, lower alkylamino, lower dialkylamino, cyano, or S(O)ₙR wherein n is 0, 1 or 2, and R is lower alkyl of one to six carbon atoms, optionally substituted phenyl, optionally substituted phenyl lower alkyl, or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano;
W is alkyl of one to seven carbon atoms, phenyl or benzyl optionally substituted with one or two lower alkyl of one to four carbon atoms, lower alkoxy of one to four carbon atoms or halo;
with the proviso that
(a) if R¹ is methoxy or ethoxy, R² is hydrogen and W is methyl; or if R¹ is methoxy, R² is methyl and W is methyl, then m is not 0; or
(b) if R³ is phenyl, phenyl lower alkyl, phenyl lower alkoxy, amino, lower alkylamino, lower dialkylamino, cyano, or S(O)ₙR, then m is not 2;
or a pharmaceutically acceptable acid addition salt thereof.

19. A compound of the formula:

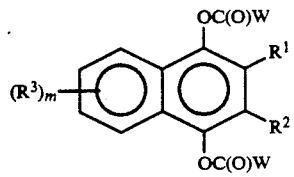

wherein:
m is 0, 1 or 2;
R¹ is alkoxy of one to twelve carbon atoms, alkylthio of one to twelve carbon atoms, phenoxy or phenylthio optionally substituted by one or two lower alkyl of one to four carbon atoms, lower alkoxy of one to four carbon atoms or halo;
R² is hydrogen, lower alkyl of one to six carbon atoms, phenyl or phenylalkyl wherein the phenyl ring of the phenylalkyl group is optionally substituted by one or two substituents selected from the group consisting of halo, lower alkyl of one to four carbon atoms or lower alkoxy of one to four carbon atoms;
R³ is halo, lower alkyl, lower alkoxy, optionally substituted phenyl, optionally substituted phenyl lower alkyl, optionally substituted phenyl lower alkoxy, amino, lower alkylamino, lower dialkylamino, cyano, or S(O)ₙR wherein n is 0, 1 or 2, and R is lower alkyl of one to six carbon atoms, optionally substituted phenyl, optionally substituted phenyl lower alkyl, or heterocyclic aryl of three to nine ring atoms containing one or two heteroatoms selected from the group consisting of nitrogen, oxygen and sulfur wherein the heterocyclic aryl is optionally substituted by one or more substituents selected from the group consisting of lower alkyl, lower alkoxy, halo and cyano;
W is alkyl of one to seven carbon atoms, phenyl or benzyl optionally substituted with one or two lower alkyl of one to four carbon atoms, lower alkoxy of one to four carbon atoms or halo;
with the proviso that
(a) if R¹ is methoxy or ethoxy, R² is hydrogen and W is methyl; or if R¹ is methoxy, R² is methyl and W is methyl, then m is not 0; or
(b) if R³ is phenyl, phenyl lower alkyl, phenyl lower alkoxy, amino, lower alkylamino, lower dialkylamino, cyano, or S(O)ₙR, then m is not 2;
or a pharmaceutically acceptable acid addition salt thereof.

20. The compound of claim 19 wherein m is 2.

21. A compound of claim 19 of the formula

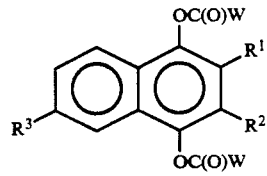

wherein R¹, R²R³ and W are as defined in claim 19.

22. A compound of claim 21 wherein R³ is selected from the group consisting of fluoro, chloro and bromo.

23. A compound of claim 21 wherein R³ is cyano.

24. The compound of claim 20 wherein W is alkyl of one to seven carbon atoms.

25. The compound of claim 24 wherein R¹ is alkoxy of one to twelve carbon atoms or alkylthio of one to twelve carbon atoms.

26. The compound of claim 25 wherein R² is hydrogen.

27. The compound of claim 25 wherein R² is lower alkyl of one to six carbon atoms, phenyl or phenylalkyl optionally substituted by one or two lower alkyl of one to four carbon atoms, lower alkoxy of one to four carbon atoms or halo.

28. The compound of claim 24 wherein R¹ is phenoxy or phenylthio optionally substituted by one or two lower alkyl of one to four carbon atoms, lower alkoxy of one to four carbon atoms or halo.

29. The compound of claim 28 wherein $R^2$ is hydrogen.

30. The compound of claim 28 wherein $R^2$ is lower alkyl of one to six carbon atoms, phenyl or phenylalkyl optionally substituted by one or two lower alkyl of one to four carbon atoms, lower alkoxy of one to four carbon atoms or halo.

31. The compound of claim 20 wherein W is phenyl or benzyl optionally substituted by one or two lower alkyl of one to four carbon atoms, lower alkoxy of one to four carbon atoms or halo.

32. The compound of claim 32 wherein $R^1$ is alkoxy of one to twelve carbon atoms or alkylthio of one to twelve carbon atoms.

33. The compound of claim 32 wherein $R^2$ is hydrogen.

34. The compound of claim 32 wherein $R^2$ is lower alkyl of one to six carbon atoms, phenyl or phenylalkyl optionally substituted by one or two lower alkyl of one to four carbon atoms, lower alkoxy of one to four carbon atoms or halo.

35. The compound of claim 31 wherein $R^1$ is phenoxy or phenylthio optionally substituted by one or two lower alkyl of one to four carbon atoms, lower alkoxy of one to four carbon atoms or halo.

36. The compound of claim 28 wherein $R^2$ is hydrogen.

37. The compound of claim 28 wherein $R^2$ is lower alkyl of one to six carbon atoms, phenyl or phenylalkyl optionally substituted by one or two lower alkyl of one to four carbon atoms, lower alkoxy of one to four carbon atoms or halo.

* * * * *